United States Patent
O'Quinn et al.

(10) Patent No.: US 7,118,583 B2
(45) Date of Patent: *Oct. 10, 2006

(54) MENISCAL SUTURING INSTRUMENT AND METHOD

(75) Inventors: Philip S. O'Quinn, Naples, FL (US); Robert M. Weber, Chino Hills, CA (US); Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 507 days.

This patent is subject to a terminal disclaimer.

(21) Appl. No.: 10/277,686

(22) Filed: Oct. 23, 2002

(65) Prior Publication Data

US 2003/0078600 A1    Apr. 24, 2003

Related U.S. Application Data

(60) Provisional application No. 60/330,490, filed on Oct. 23, 2001.

(51) Int. Cl.
    *A61B 17/10*    (2006.01)
(52) U.S. Cl. ............... 606/139; 606/144; 606/148; 606/223
(58) Field of Classification Search ............... 606/139, 606/144, 148, 223
    See application file for complete search history.

(56) References Cited

U.S. PATENT DOCUMENTS

| | | | |
|---|---|---|---|
| 1,822,330 A | 9/1931 | George | |
| 2,738,790 A * | 3/1956 | Todt, Sr. et al. | 606/145 |
| 5,059,201 A * | 10/1991 | Asnis | 606/144 |
| 5,336,229 A * | 8/1994 | Noda | 606/144 |
| 5,431,666 A * | 7/1995 | Sauer et al. | 606/139 |
| 5,522,820 A * | 6/1996 | Caspari et al. | 606/148 |
| 5,562,686 A * | 10/1996 | Sauer et al. | 606/144 |
| 5,665,096 A * | 9/1997 | Yoon | 606/139 |
| 6,056,778 A | 5/2000 | Grafton et al. | |
| 6,533,796 B1 * | 3/2003 | Sauer et al. | 606/144 |
| 6,770,084 B1 * | 8/2004 | Bain et al. | 606/144 |
| 6,893,448 B1 * | 5/2005 | O'Quinn et al. | 606/139 |

FOREIGN PATENT DOCUMENTS

| | | |
|---|---|---|
| SU | XP002224844 | 5/1977 |
| WO | WO 91 06247 A | 5/1991 |
| WO | WO 99 47050 A | 9/1999 |

* cited by examiner

*Primary Examiner*—Anhtuan T. Nguyen
*Assistant Examiner*—Darwin P. Erezo
(74) *Attorney, Agent, or Firm*—Dickstein Shapiro LLP

(57) ABSTRACT

An instrument for surgical suturing includes a shaft, and a needle disposed slidably for longitudinal travel with respect to the shaft. A prong formed on one end of the shaft projects across a longitudinal axis of the needle and has an opening formed through the prong that provides a clearance through which a tip portion of the needle passes when it is advanced. Slots formed on a surface of the prong facing the shaft releasably hold suture across the opening. Advancing the needle through the clearance allows a hook formed on the tip of the needle to capture the suture. Once withdrawn, the needle draws the suture back through tissue pierced during advancement. The suture is released from the slots and drawn back through the tissue for further knot tying and suturing to effect the tissue repairs.

4 Claims, 3 Drawing Sheets

MENISCAL SUTURING INSTRUMENT AND METHOD

This application claims the benefit of U.S. Provisional Application No. 60/330,490, filed Oct. 23, 2001.

BACKGROUND OF THE INVENTION

1. Field of the Invention

The present invention relates to endoscopic suturing, and more particularly to instruments for endoscopic treatment of meniscal tears.

2. Description of the Related Art

The menisci are crescent-shaped structures of fibrocartilaginous tissue located in the knee between the condyles of the tibia and the femur. The menisci, which are actually extensions of the tibia, serve to deepen the tibial plateau to better accommodate the opposing curvature of the articulating surface of the femoral condyle.

A typical injury to the knee is a meniscal tear, which can occur, for example, when the meniscus is displaced and caught between the femoral and tibial condyles during a sudden change of movement of the knee involving a combined flexion-rotation or extension-rotation motion. Meniscal tears were originally treated by removing the meniscus in an operation called a meniscectomy. However, results showed that removing the meniscus, either entirely or even partially, resulted in degenerative arthritis and instability in the knee.

As a result of the above-described complications, surgeons began treating meniscus tears with suturing techniques to retain as much of the meniscus as possible. However, suturing of a meniscal tear, like a meniscectomy, was originally an open technique, requiring a large incision and consequently longer periods of rehabilitation and recovery. Advances in instrumentation ultimately led to arthroscopic meniscal repair using long needles for passing suture through the tear.

More recently, various tacks, screws and implants have been developed for meniscal repair, which can be used arthroscopically and simplify the surgery by eliminating the need for suturing altogether. For example, U.S. Pat. No. 6,056,778, assigned to the assignee of the present application, discloses a meniscal repair device provided with a plurality of opposed crescent-shaped grooves which can be used to mend meniscal tears.

Some surgeons, however, prefer to repair meniscal tears arthroscopically using suture, but seek to avoid the difficulties associated with using long needles. Accordingly, it would be desirable to provide an instrument and method for repairing torn meniscal tissue which facilitate the passing of suture through a torn meniscus arthroscopically.

SUMMARY OF THE INVENTION

The present invention provides an instrument and method for suturing tissue arthroscopically, in particular for repairing torn meniscal tissue.

The instrument features a needle slidably disposed in a tubular shaft. The needle is advanced from the shaft to pierce through the tissue to be repaired. With continued advancement, a hook disposed at the end of the needle engages a length of suture supported on a prong that extends from the end of the instrument shaft, ahead of the advancing needle. The needle then is withdrawn, drawing a captured loop of the suture back through the pierced tissue. The suture loop is available for subsequent suturing or knot tying.

More specifically, tissue suturing begins by presenting the instrument, loaded with suture, into a human knee, for example. The operative end of the instrument is positioned, with the needle withdrawn, proximate the meniscal tissue to be repaired. The needle then is advanced to pierce the tissue. Further advancement of the needle brings it clear of the pierced tissue to approach a length of suture supported in a slot on the extended prong at the end of the instrument. The hook formed toward the tip of the needle captures the suture. Drawing the needle back pulls a loop of the captured suture through the tissue.

Operation of the instrument is facilitated by additional features of the invention. One-handed manipulation of the instrument, for example, is simplified by a thumb slide that is provided on a handle secured to the back end of the tube. In addition, the needle may be spring loaded to assist in drawing the needle back through the tube. Accordingly, the instrument can be operated using one hand, the thumb of the hand working to advance the needle through the tube to pierce tissue, capture the suture, and withdraw the captured suture back through the tissue. In addition, the needle can be configured to be withdrawn completely from the instrument to facilitate suture manipulation and withdrawal of the instrument from the patient. Further, the instrument can be made to be disposable, and can be manufactured with a malleable shaft which can be bent into various configurations to provide further direction control of suture placement.

Other features and advantages of the present invention will become apparent from the following description of the invention which refers to the accompanying drawings.

BRIEF DESCRIPTION OF THE DRAWINGS

FIG. 4 is a side elevation of a working end of the instrument of FIG. 1.

DETAILED DESCRIPTION OF THE PREFERRED EMBODIMENT

Figure 1:
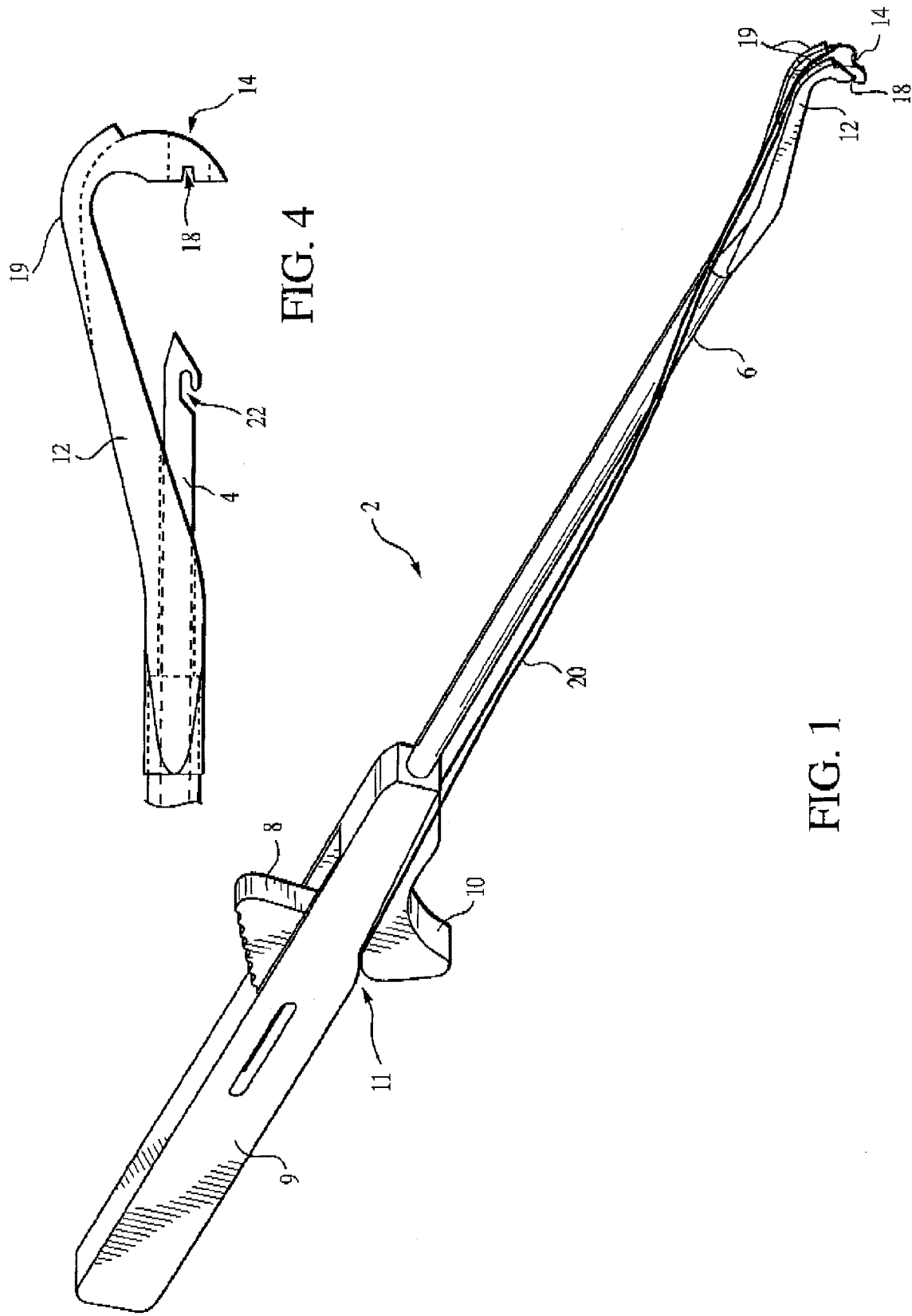
FIG. 1 is a perspective view of a tissue suturing instrument according to a preferred embodiment of the present invention.

Referring initially to FIG. 1, a tissue suturing device 2 according to a preferred embodiment of the present invention includes a needle 4 (FIG. 2) that slides inside of a tubular shaft 6. Optionally, at least a portion of shaft 6 can be bendable, formed of a malleable material, for example, to facilitate directional control of suture placement. The needle is operated by a thumb slide 8 disposed on handle 9. A finger support 10 is provided for ease of handling. A suture notch 11 is used to secure loose ends of suture 20.

Figure 2:
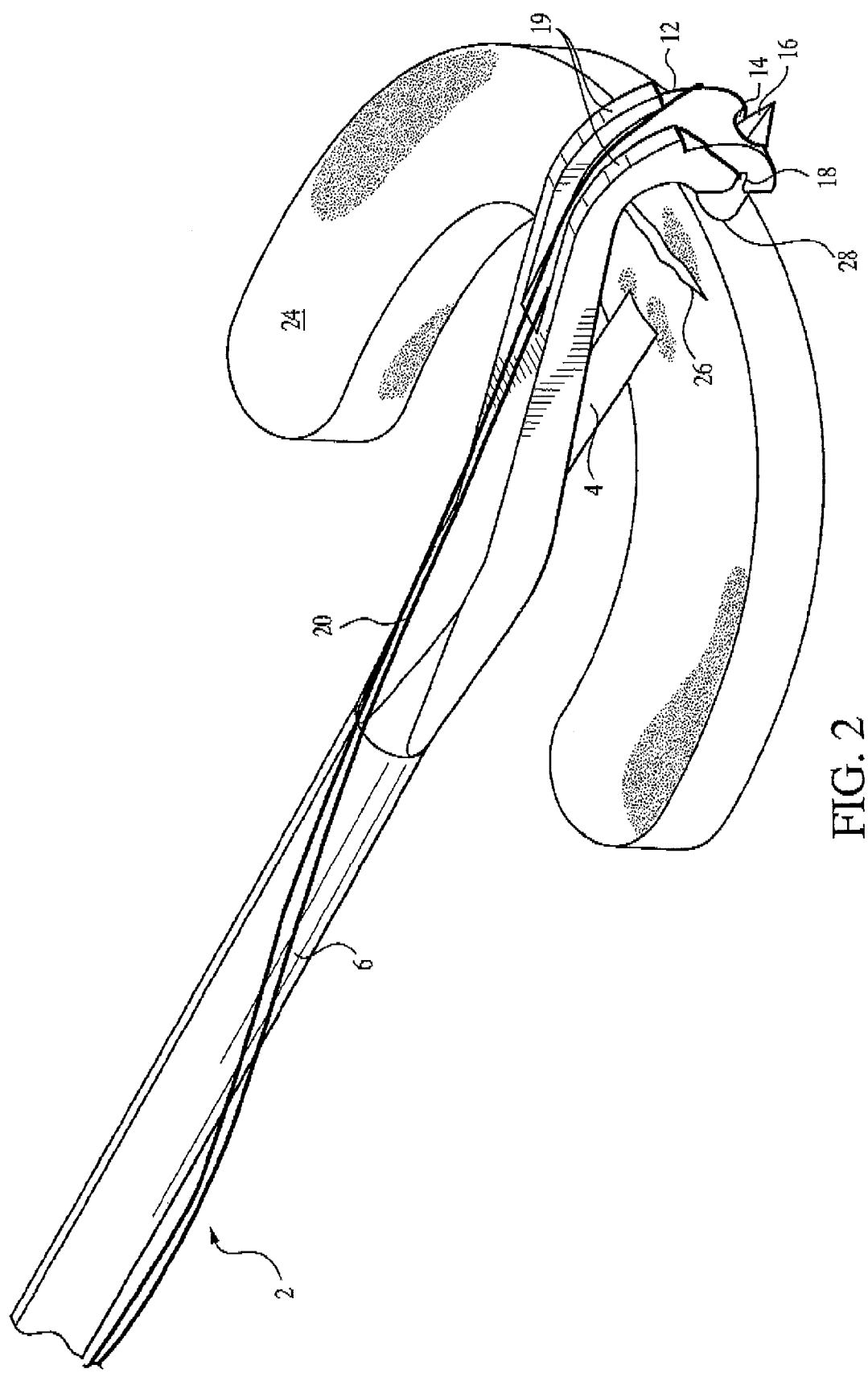
FIG. 2 is a detailed perspective view of the operative end of the instrument of FIG. 1 being applied in a surgical step of torn tissue repair according to the present invention.
Figure 3:
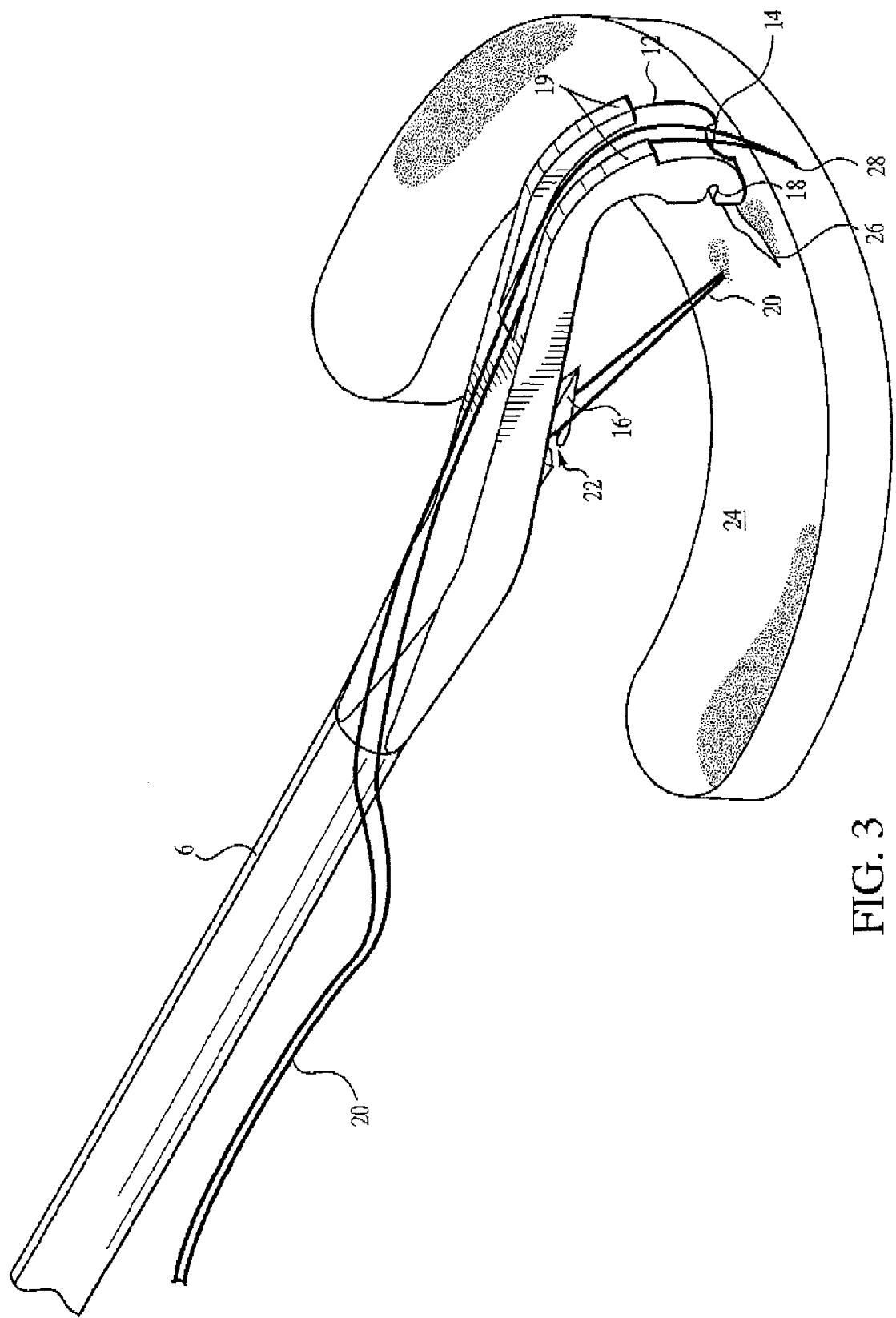
FIG. 3 is a detailed view of the operative end of the instrument of FIG. 1 being used in a further surgical step of torn tissue repair according to the present invention.

The working end of tube 6 is provided with an extended prong 12, shown in greater detail in FIGS. 2–4. Prong 12 takes a flattened form that projects over and in advance of an extended end of the needle 4. An opening 14 provides a clearance in the distal end of prong 12. Manipulation of the instrument 2 with the thumb of one hand advances needle 4. The opening 14 is aligned to provide passage for a tip portion of needle 4 when the needle is advanced.

A point 16 of the needle projects upon advancement through opening 14 to engage a length of suture, as follows: A slot 18 formed in the prong 12 holds braided suture 20. Referring also to FIG. 3, slot 18 intersects opening 14. Suture 20 passes up through a channel between ridges 19 and is held under tension using suture notch 11. Accordingly, a portion of suture 20 held in slot 18 transects opening 14. A hook 22 formed in the end of the needle 4 captures the portion of suture 20 when the needle is advanced through the opening.

More specifically, referring to FIG. 2, instrument 2 is brought by way of arthroscopic or open surgical means to tissue, such as meniscus 24, which is in need of repair due to a tear 26, for example. Braided suture 20 preferably is preloaded into slot 18. Needle 4 is advanced through the meniscal tissue and across the tear, piercing the meniscus 24 to form exit hole 28.

As the tip 16 of needle 4 passes through opening 14, hook 22 formed in the end of the needle captures the suture, and a loop of suture is drawn back through meniscus 24 as the needle is withdrawn by way of thumb slide 8, assisted by the retrograde urging of an optional spring. The loop of suture accordingly is available for further suturing and knot tying.

While preferred embodiments of the invention has been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed as new and desired to be protected by Letters Patent of the United States is:

1. An instrument for surgical suturing of a meniscal tear, comprising:
    a shaft;
    a needle disposed slidably for longitudinal travel with respect to the shaft;
    a curved prong on one end of the shaft, the prong projecting across a longitudinal axis of the needle and having an opening formed through the prong that provides a clearance through which a tip portion of the needle passes when it is advanced;
    open slots formed on an inner side of the prong, said open slots facing the end of the shaft and retaining a loop of suture on the inner surface of the prong facing the end of the shaft such that the suture extends across the opening formed through the prong; and
    a suture channel formed on a top outer surface of the prong and extending longitudinally with respect to the shaft,
    wherein the suture loop is retained in the open slots of the prong by passing suture strands extending from said loop separately around respective opposite sides of the prong and together through the suture channel formed on the top outer surface of the prong.

2. The instrument of claim 1, further comprising a handle, wherein the shaft is fixed nonslidably to the handle.

3. A hand instrument for suturing a mensical tear, the hand instrument comprising:
    a tubular shaft having proximal and distal ends;
    a needle disposed slidably within the tubular shaft;
    a prong formed on the distal end of the tubular shaft including open slots for holding a length of suture on a proximal face of the prong in a sliding path of the needle, such that a hook formed on the needle captures the length of suture and, upon proximal movement of the needle, the suture is released from the proximal face prong; and
    a suture channel formed on a top outer surface of the prong and extending longitudinally with respect to the shaft;
    wherein the length of suture is retained in the open slots of the prong by passing opposite strands of said suture separately around respective opposite sides of the prong and together through the suture channel formed on the top outer surface of the prong.

4. A method for suturing meniscal tears using a hand instrument having a tubular shaft, a needle slidably disposed in the tubular shaft and having a hook formed on the distal end, and a prong formed on a distal end of the tubular shaft holding a length of suture in open slots formed on a proximal face of the prong, said open slots facing the end of the shaft, the suture being held in the slots by passing opposite strands of the suture separately back around respective opposite sides of the prong, then together up through a longitudinal channel formed on a top outer surface of the prong above the slots, the method comprising the steps of:
    proximating a meniscal tear with the hand instrument;
    advancing the needle through meniscal tissue on opposite side of the tear;
    engaging the length of suture extending through the open slots with the hook in the needle; and
    sliding the needle proximally such that the length of suture engaged by the hook is released from the open slots formed on the proximal face of the prong and drawn back away from the prong and through the meniscal tissue on opposite sides of the tear.

* * * * *